(12) United States Patent
Penn

(10) Patent No.: US 9,232,827 B1
(45) Date of Patent: Jan. 12, 2016

(54) ORTHOPEDIC PROTECTIVE HELMET

(75) Inventor: John Penn, Orlando, FL (US)

(73) Assignee: ORTHOMERICA PRODUCTS, INC., Orlando, FL (US)

(*) Notice: Subject to any disclaimer, the term of this patent is extended or adjusted under 35 U.S.C. 154(b) by 55 days.

(21) Appl. No.: 13/244,012

(22) Filed: Sep. 23, 2011

Related U.S. Application Data

(60) Provisional application No. 61/386,417, filed on Sep. 24, 2010.

(51) Int. Cl.
A42B 3/00 (2006.01)
A42B 3/32 (2006.01)

(52) U.S. Cl.
CPC .................................... *A42B 3/324* (2013.01)

(58) Field of Classification Search
CPC ........................................................ A42B 3/00
USPC ............ 2/410, 411, 412, 414, 417, 418, 420, 2/421, 425; 128/97.1, 857, 864–866; 602/17
See application file for complete search history.

(56) References Cited

U.S. PATENT DOCUMENTS

| | | | |
|---|---|---|---|
| 4,397,045 A * | 8/1983 | Schonwetter et al. | 2/5 |
| 4,745,637 A | 5/1988 | Steele et al. | |
| 4,845,786 A | 7/1989 | Chiarella | |
| 4,847,921 A | 7/1989 | Leutholt et al. | |
| 4,988,740 A | 1/1991 | Walter et al. | |
| 5,075,903 A | 12/1991 | Richoux | |
| 5,887,289 A * | 3/1999 | Theoret | 2/425 |
| 6,625,820 B1 * | 9/2003 | Lampe | 2/425 |
| 2002/0002733 A1 * | 1/2002 | Keen | 2/425 |
| 2006/0168712 A1 * | 8/2006 | Mazzoccoli et al. | 2/411 |
| 2008/0172779 A1 | 7/2008 | Ferguson | |

* cited by examiner

*Primary Examiner* — Clinton T Ostrup
*Assistant Examiner* — Sally Haden

(57) ABSTRACT

A cranial protective helmet having a pair of components made of an exterior hard plastic shell with sufficient flexibility to accommodate comfort for the patient with interior cushioning liners conforming to a side of the patient's skull. Each component of the helmet can conform to a side of the patient's head and accommodate an insertion of the patient's head by relative movement with one or more fastener units securing the helmet components to the patient. Openings can be provided to accommodate monitoring instrumentation after a craniectomy operation. The components can be separate or minimally connected to enable a rotational opening. Fastener units can provide a secure connection of the components and an elastic attachment about the patient's head.

4 Claims, 19 Drawing Sheets

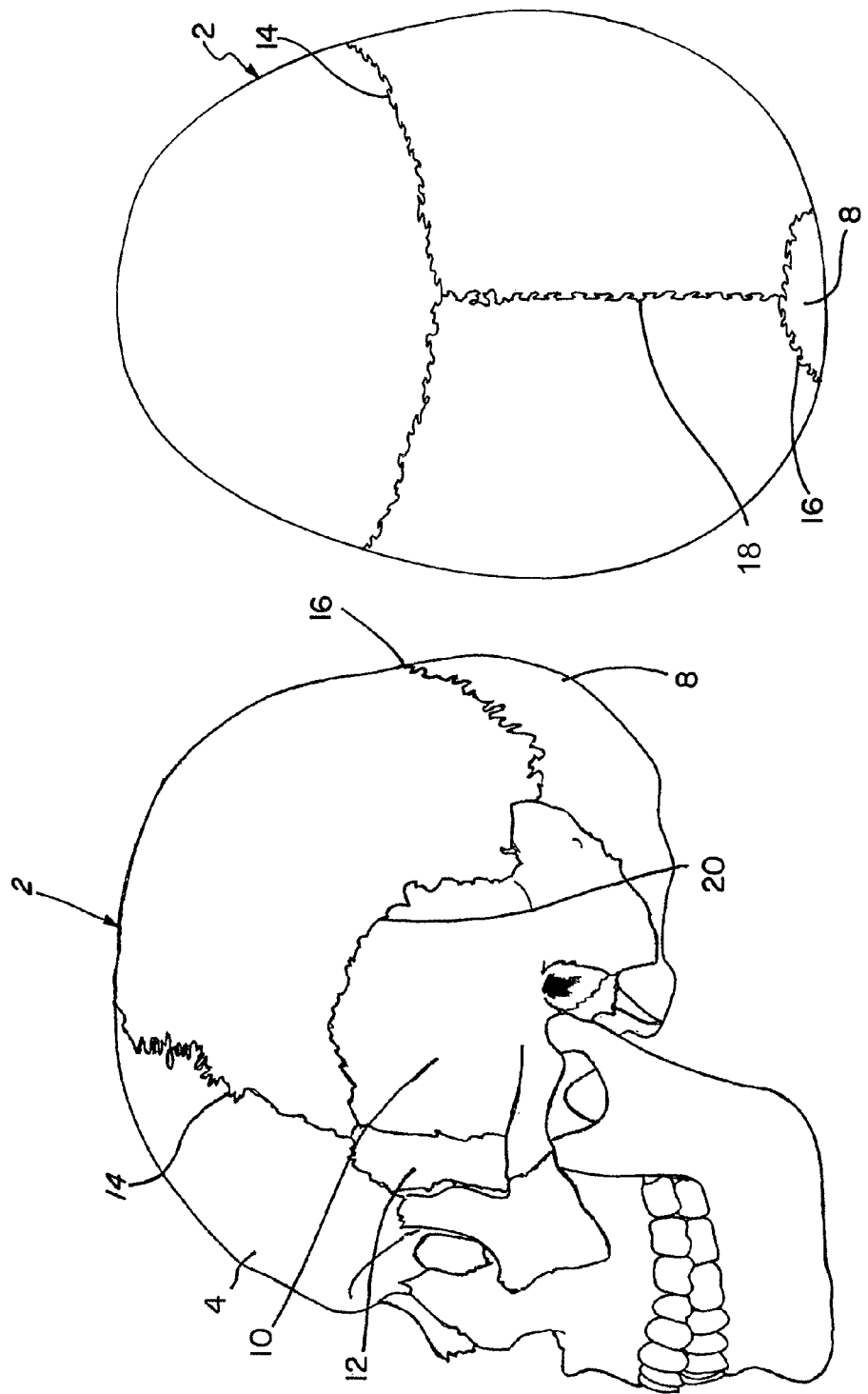

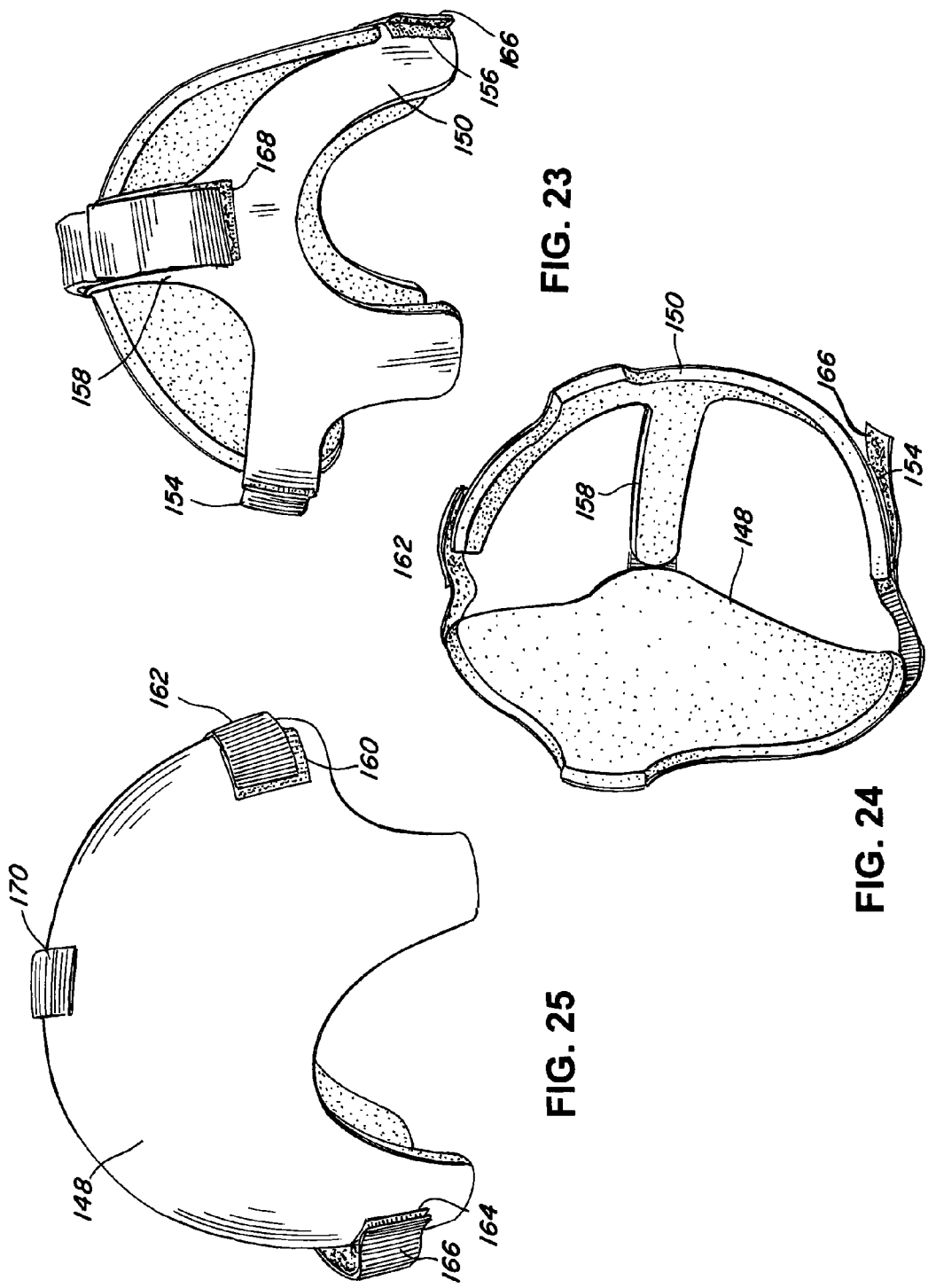

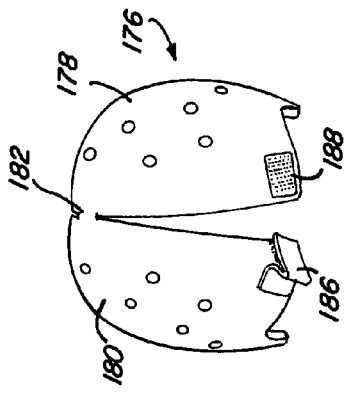
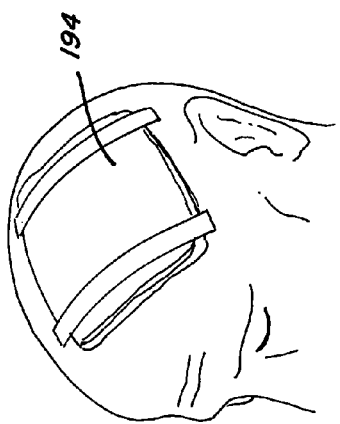
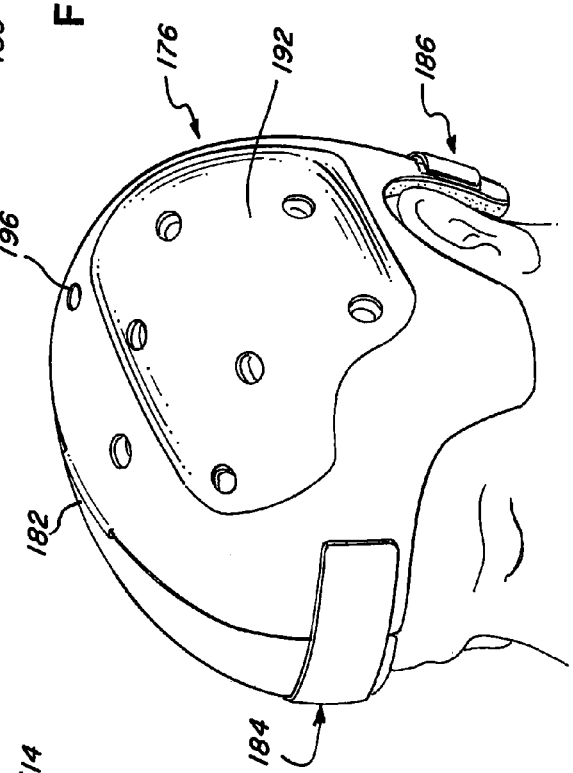
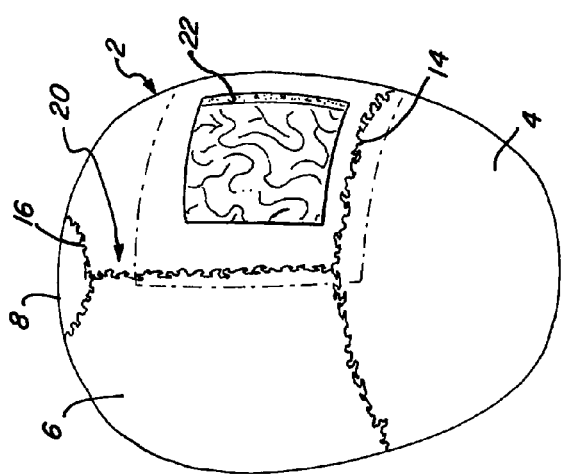
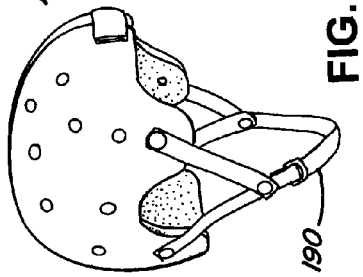
FIG. 29
FIG. 27
FIG. 28
FIG. 26
FIG. 30

ORTHOPEDIC PROTECTIVE HELMET

CROSS-REFERENCE TO RELATED APPLICATION

The present application claims priority from a provisional application No. 61/386,417 filed on Sep. 24, 2010.

BACKGROUND OF THE INVENTION

1. Field of the Invention

In the orthopedic field there is frequently a requirement to provide a protective covering such as a helmet to protect a patient's head, for example after cranial surgery, such a protective helmet assists in preventing injury to a decompressed craniectomy surgical site where a portion of the skull has been removed to treat traumatic brain injury, cerebral edema and elevated intracranial pressure.

2. Description of Related Art

Protective helmets for children and particularly infants with a plagiocaphalic cranium are found in U.S. Pat. No. 4,776,324 and U.S. Pat. No. 6,428,494. A purportedly cosmetically acceptable cranial prosthesis is disclosed in U.S. Pat. No. 4,809,690, U.S. Pat. No. 5,218,975 and U.S. Pat. No. 5,549,678.

The human skull is initially formed from a substantial number of individual bone elements. As the child grows during the pregnancy and the first 18 months after birth, an endocrhondra ossification occurs and the respective bony elements will tend to fuse together into a solid bone that forms a cranial vault for the brain. Thus, the cranial anatomy basically includes a frontal bone that extends from the eye cavity or supra orbital process upward to the top of the skull where a pair of parietal bones on either side of the skull are fused together with the frontal bone by a coronal suture. A sagittal suture joins the respective parietal bones extending rearward until they meet a rear occipital bone with the junction of the parietal bones being defined by a lambdoidal suture. On either side of both the frontal bone and the parietal bones are a respective temporal bone and sphenoid bone that are joined by a squamosal suture. The final bone fusion of the skull occurs in adulthood and provides a relatively non-deformable protection from the brain during normal activities.

A traumatic injury such as a severe fall, auto accident or gunshot wound can compromise the skull. Additionally, a stroke patient can be subject to cerebral edema and elevated intracranial pressures necessitating an intervention and a removal of a portion of the skull to allow space for the swelling brain to expand in an effort to prevent brain tissue damage with a potential compromise of cerebral circulation and function.

In such a post-operative environment, there is still a need to provide improvements in cranial protective systems such as an orthopedic protective helmet while facilitating intensive care of the patient to accommodate surgical dressings and post operative treatments including monitoring intracranial pressure sensors and cranial fluid release in a relatively lightweight orthopedic helmet.

SUMMARY OF THE INVENTION

The present invention provides a relatively lightweight flexible plastic shell that can conform to a human skull either by custom manufacturing to specifications of a scanned patient's head or by providing sets of prefabricated helmets for various sizes of protective helmets from pediatric through adult. The helmet protection provides particular advantages against low impact forces that can be distributed like a shock absorber across the entire surface without cracking or penetration of the helmet. A closed shell foam can line the inside of a plastic exterior shell of the helmet to cushion the head and absorb impact energy. The helmet design is equipped with an easy to adjust strap or a particular configuration of straps that can minimize a need for chin straps. The various embodiments of our protective helmets can facilitate both bed rest and ambulatory movement of the patient.

The cranial protective helmet of the present invention can include in one embodiment, a first component having an exterior hard plastic shell and an interior cushioning liner of a configuration to conform to a portion of an outside surface of a user's head from a frontal to an occipital bone and a second component having an exterior hard plastic shell and an interior cushioning liner of a configuration to conform to a portion of an outside surface of a user's head from a frontal bone to an occipital bone. A first adjustable fastener unit can extend across a portion of the first component and a portion of the second component that cover the frontal bone to permit a sizing adjustment to the user and a second adjustable fastener unit extending across a portion of the first component and a portion of the second component that cover the occipital bone, to permit a further sizing adjustment to the user.

Another embodiment provides a cranial protective helmet having an exterior hard plastic shell and an interior cushioning liner of a configuration to conform to a portion of an outside surface of a user's head from a frontal bone to an occipital bone. The plastic shell and cushioning liner is divided into a first component and a second component that are pivotally connected to each other to enable rotation to a spread open position for insertion on a user's head. A first adjustable fastener unit, extends across a portion of the first component and a portion of the second component to enable a sizing adjustment to the user's head. A second adjustable fastener unit extending across a portion of the first component and a portion of a second component enables a further sizing adjustment to the user's head.

In a further embodiment, one of the first and second components of the protective helmet has a smaller exterior surface area than the other component and further can have a third adjustable fastener unit, extending across a portion of the first component and a portion of the second component in a location between the first and second adjustable fastener unit to permit a sizing adjustment.

An alternative embodiment provides a cranial protective helmet of an exterior semi-rigid plastic shell and an interior cushioning liner mounted within the exterior hard plastic shell of a configuration that conforms to a portion of an outside surface of a user's head and to extend over a portion of a frontal bone and across portions of parietal bones. The plastic shell and liner can have a U-shaped configuration with side portions cantilevered from a front portion extending over the frontal bone. A first adjustable fastener unit can extend across the open U-shaped configuration to enable a retention of the shell on the user's head. A second adjustable fastener unit can be attached to the shell at a location for extending from one side portion to another side portion over a sagittal suture of the parietal bones of the user. The fastener units can have a degree of elasticity to provide a comfortable fit.

Another embodiment of the present invention provides a cranial protective helmet with an exterior hard plastic shell and an interior liner of a configuration to conform to a portion of the outside surface of a user's head from a frontal bone to an occipital bone. This embodiment, like the other embodiments, can utilize a perimeter edge configured to inhibit both migration and rotation of the protective helmet relative to the user's head. The perimeter can have a concave configuration to accommodate the user's ears with further extensions on either side of the ear to enable securement of the helmet to the user's head. As a further modified embodiment, the first and second component can be symmetrical with a hinge member positioned to enable rotation approximately along a sagittal suture to the user's head to enable an opening of the respective first and second components for easy mounting on a user's head.

A further embodiment modification can utilize a first component and a second component that are asymmetrical with a hinge member positioned to enable rotation approximately traverse to a sagittal suture of the user's head.

The plastic shell and cushioning liner can include a plurality of ventilation holes where necessary in each of the embodiments to assist in cooling and removal of heat from the user's head. While other adjustable fastening units can be utilized, a hook and nap arrangement of a flexible strap and an anchor patch mounted on one of the components with the flexible strap riveted or alternatively anchored by a second anchor patch is provided on the other component.

The cranial protective helmets of the various embodiments can be custom manufactured from specific dimensions of a scan patient's head or alternatively, can be prefabricated helmets of different sizes that can be subsequently modified by an orthotist to accommodate the particular patient.

The cranial protective helmets are preferably of a hard but relatively flexible plastic shell or shell components to ensure a lightweight configuration and openings can be provided on the various components to provide additional ventilation and easy access for intracranial monitoring sensors such as pressure and oxygen sensors and fluid relief.

Additionally, with a customized scan of the patient's head, a depressed configuration of the cranial anatomy indicating the removal of bone can be identified and a corresponding component of both the exterior hard plastic shell and the interior cushioning liner can be expanded, for example by enlarging the perimeter of the depression area by ½ inch and elevating the exterior hard plastic shell and the interior cushioning liner by ½ inch from the head to facilitate providing room for any bandages and dressings of the wound so that unnecessary pressure is not applied to the brain at the site of the injury.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 1 is a schematic of a side view of a human skull;

FIG. 2 is a plan view of the top of the human skull;

FIG. 23 is a left hand side view of the protective helmet of FIG. 21;

FIG. 24 is a bottom view of the two shell components of FIG. 22;

FIG. 25 is a right hand side view of the protective helmet of FIG. 22;

FIG. 26 is a schematic representation of the surface of a skull with a segment of the skull removed;

FIG. 27 is a partial schematic representation of a patient with bandaging over the surgical site;

FIG. 28 is a perspective view of a protective helmet;

FIG. 29 is a rear schematic view of the protective helmet of FIG. 28 rotated about a living hinge for mounting on a patient;

FIG. 30 is a side perspective view of a protective helmet of FIG. 28 with a chin strap;

DETAILED DESCRIPTION OF THE PREFERRED EMBODIMENTS

Figure 3:
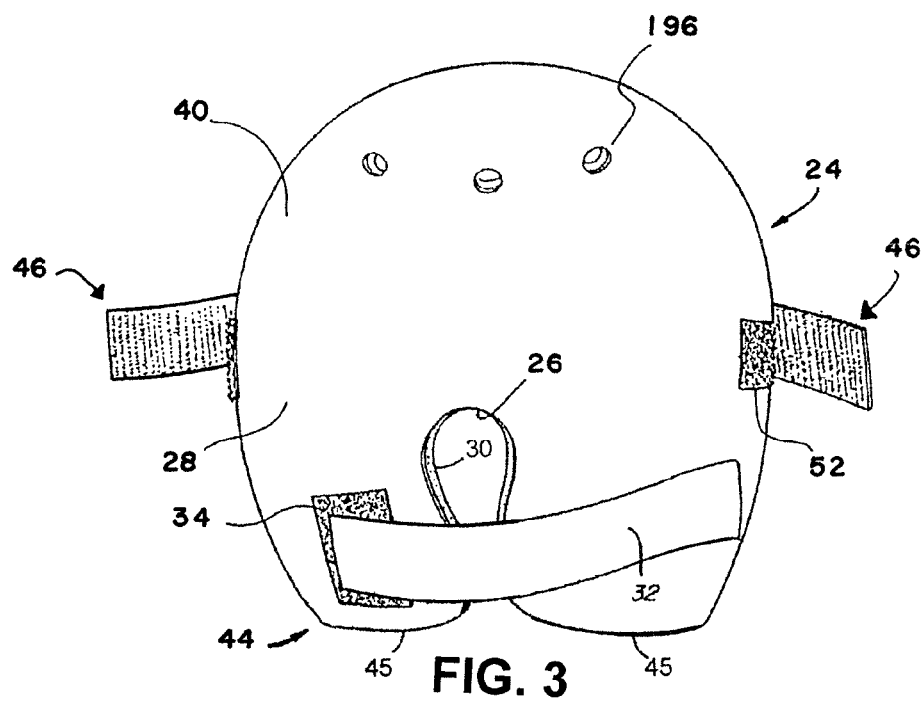
FIG. 3 is a rear view of a protective helmet of one embodiment of the present invention.

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

The cranial protective helmets of the present invention are usually fitted by an orthotist or clinician specifically trained in the use of such devices. The orthosis or protective helmet comes in contact with intact skin and uses materials that are known in this industry to be safe and biocompatible. The cranial protective helmets of the present invention can be either prefabricated in various sizes or can be customized by measurements taken of a patient's skull.

For example, for customized cranial protective helmets, a patient's head can be scanned with a video camera or a laser scan to determine the topography of the patient's head. Using these dimensional measurements, a positive mold can initially be formed with a multi-axis router, and then subsequently finished by grinding to provide a desired mold to conform to the specific requirements of the patient.

Alternatively, for prefabricated cranial protective helmets, a mold of a human head having known generic measurements can be utilized as opposed to the customized scan measurements of a specific patient. In both embodiments a positive mold is formed which then can be used in a thermal forming procedure by connecting the mold to a vacuum source and applying a fabric over the mold to enhance airflow. A layer of foam in the form of a sheet of approximately ½ inch in thickness can be appropriately heated and positioned directly over the mold.

Subsequently, a mesh material can be placed over the formed foam cushioning layer with an appropriate adhesive, and a sheet of approximately 3/16 inch in thickness of a copolymer plastic can be heated to a thermal forming temperature. The plastic sheet is then appropriately placed over the mold so that it is sealed and extends completely over the entire surface of the mold and is sealed around a vacuum plate. When the vacuum is applied, the plastic sheet is contracted to snugly fit over the foam covered mold. The plastic is allowed to cool and then removed along with the foam from the mold.

By cutting, the resulting plastic and foam shell is trimmed so trim lines can be marked on the mold and edges can be buffed to a smooth shape. Subsequently, one or more fastener units such as straps can be adhered to the plastic shell by adhesive or a nap and hook material such as Velcro™ or alternatively riveted to the plastic shell.

Referring to FIG. 1, a cranial anatomy of a human skull 2 is disclosed and includes a frontal bone 4, a pair of parietal bones 6 on either side of the human skull 2, a rear occipital bone 8, a pair of temporal bones 10 and a pair of sphenoid bones 12.

During the process of endocrhondra ossification, as the individual bone elements knit together, the frontal bone that extends across the forehead and eye cavities is joined at the parietal bones 6 by a coronal suture. The parietal bones 6 are joined across the top of the skull extending symmetrically down the middle of the skull from the frontal bone 4 to the occipital bone 8 by a sagittal suture 18. The occipital bone 8 is joined to the parietal bones 6 by the lamboidal suture 16, and the respect side spagnoid bones 12 and temporal bones 10 are joined to the respective frontal bone and parietal bones by a squamosal suture 20.

FIG. 2 is a top plan view of the skull 2.

The present invention is directed to providing a relatively lightweight flexible plastic shell that can protect the patient and the brain against low impact forces by distributing the force across the helmet structure with a closed shell foam liner cushioning the head and absorbing impact energy.

Referring to FIG. 3, a rear view of a protective helmet 24 showing a teardrop curved opening 26 in the respective exterior plastic shell 28 and a foam cushion liner 30 is shown.

The exterior plastic shell 28 can be made from a plastic copolymer with a tension strength of approximately 3100 psi pursuant to an ASTMD 638 testing method with a tension elongation before breakpoint of 240%. Thus, a relatively flexible helmet can be formed with a Durometer hardness of approximately 60 pursuant to an ASTMD 2240 testing method.

The liner 30 can be formed from a cross length foam having fine cells such as Volara™ from Sekisui Volter LLC. The foam liner 30 can be laminated into the exterior plastic shell 28 to provide a non-toxic structure that can be heat drawn with a vacuum forming capability. A plurality of ventilating holes 196 of approximately ¼ inch in diameter can be employed across the protective helmet 24 to penetrate through the exterior plastic shell 28 and the liner 30 to keep the heat generated by the patient, manageable.

The exterior plastic shell 28 has the thickness of approximately 3/64 inches to 3/32 inches and as described above, can be thermoformed into the desired shape on a mold providing the shape of the human head. The interior liner of a foam closed cell sheet has the capability of wicking away moisture and providing flexibility for conforming with a patient's head.

In FIG. 3, an arrangement of Velcro™ nap and hook components such as a strap 32 and an anchor patch member 34 can be mounted on the exterior plastic shell 28 to form a fastener unit.

As seen in FIG. 3, the strap 32 can be anchored at one end to the plastic shell 28 and can be pulled across the teardrop opening 26 for anchoring on the anchor patch member 34. The teardrop posterior opening 26 forms an upper hemispherical opening that permits a relative adjustment on the plastic shell 28 for retention of the protective helmet 24 without the necessity of having a chin strap. Thus, the protective helmet 24, when properly fitted to the patient, can be locked by the adjustable rear teardrop opening 26 to enable the trim line 45 of the helmet 24 to be adjusted below the mastoids of the patient's head.

Figure 4:
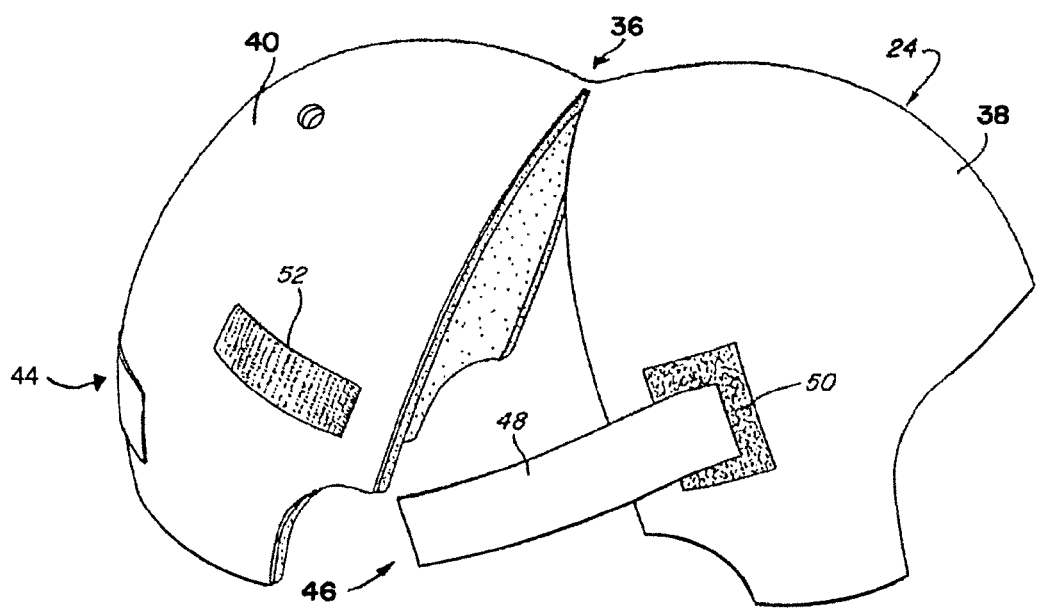
FIG. 4 is the protective helmet of FIG. 3 spread open around a living hinge to assist in mounting on a patient.

In FIG. 4, the protective helmet 24 is hinged at the top, for example by a living plastic hinge as known in the art, so that a hinge member 36 is formed for connecting each half of protective helmet 24. Alternative forms of hinges where a connection can be made so that a first component 38 extending across a frontal bone and a portion of the two parietal bones of the user can easily be mounted while a second helmet component 40 will extend across the parietal bones and extend downward across the occipital bones. The sphenoid bones and temporal bones will also be equally covered on either side. An opening on the lower perimeter of both the first component and the second component is provided so that an ear opening 42 can be formed when combined together, as shown in FIG. 5.

As shown in FIG. 3, a third adjustable fastener unit 44, extending across a portion of the second component 40 of the protective helmet 24, permits a sizing adjustment of the trim line 45 on the user.

Figure 5:
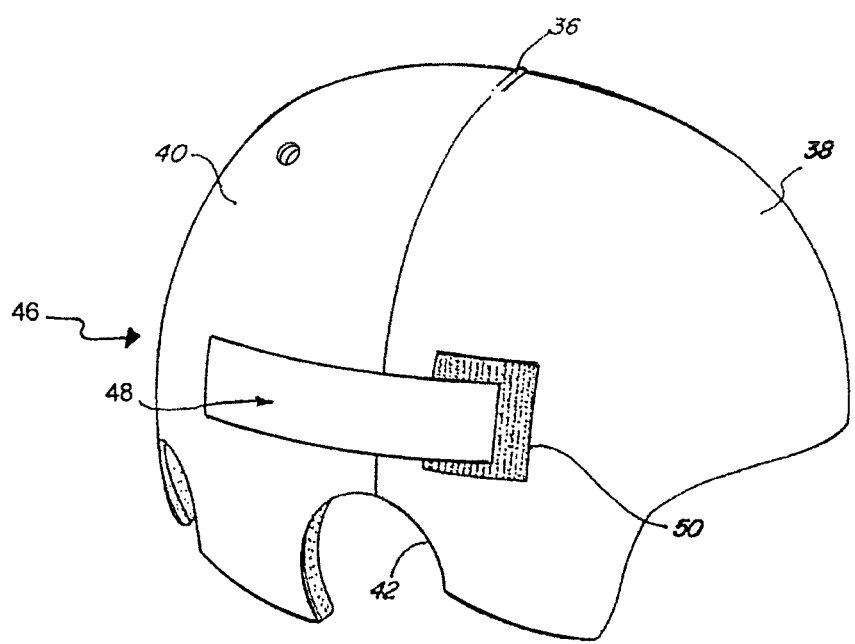
FIG. 5 is a prospective side view of the protective helmet of FIG. 3.

A first and second adjustable fastening units 46 with a fastening strap 48 and an anchor patch member 50 are shown in FIG. 5. As can be appreciated, the closing of the first component 38 and the second component 40 about the patient's head is accomplished and the respective pair of first and second adjustable fastening units 46 on either side of the protective helmet 24 are then closed. Finally, the third adjustable fastening unit 44 can be tightened to securely attach the helmet to the patient's head.

Velcro™ straps 32 and 48 can function as fastener straps although other fastener units can be used within this industry. The fastening straps 32 and 38 can have a mushroom hook such as model number Hook P87 with a peel strength of 3.0 psi, a sheer strength lengthwise of 80 psi and a tensioning strength of 18 psi. The adhesive patch of woven material or anchor patch members 34 and 50 can be adhesively adhered directly to the side of the protective helmet 24 and rear of the helmet. A quadralobel Mushroom Hook and Loop 1000 from Velcro™ USA, Inc. can be adhered to a central part of the woven material to provide a very strong retention base with a strap. As a consequence, it is not necessary to use rivets or other fasteners to facilitate a manufacturing of the protective helmet. The other side of the strap has conventional hook configurations on the anchor patch member 52 that can be adjustably and repeatedly mounted to a strip of woven nap material held by adhesive to the surface of the protective helmet 24. The straps can have an elastic ability.

In FIG. 5, the respective first component 38 and second component 40 is divided on either side of the living hinge 36 to extend across the skull to respective ear openings 42 in this perspective view.

Figure 6:
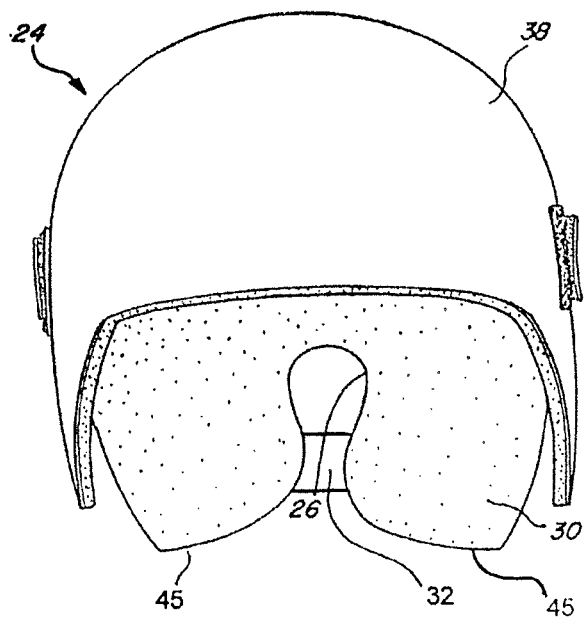
FIG. 6 is a front elevational view of the protective helmet of FIG. 3.

FIG. 6 discloses the protective helmet 24 in a frontal view and the teardrop opening 26 can be clearly seen with the posterior trim line 45 designed to minimize rotation and migration while the patient is lying on his/her back.

Figure 7:
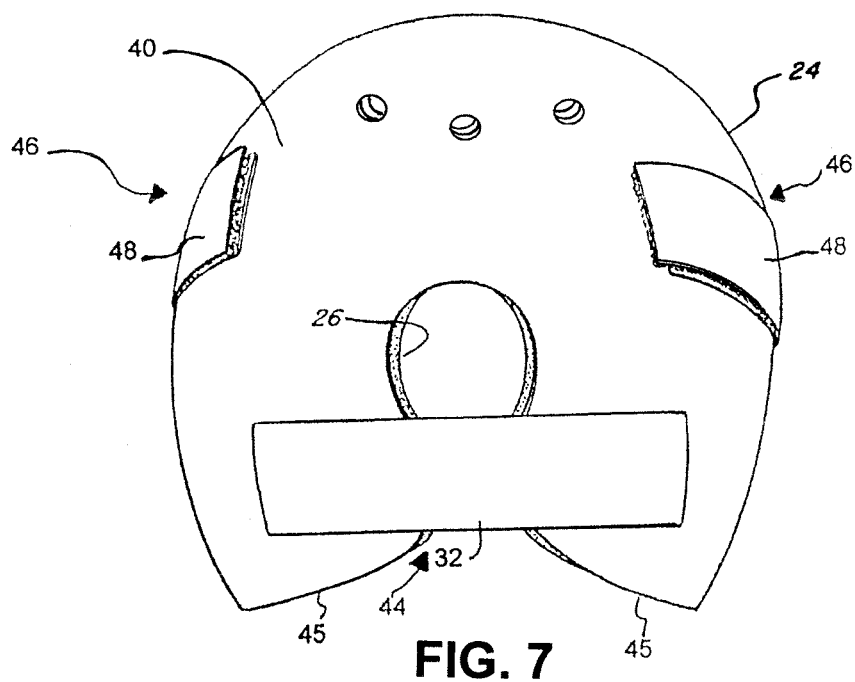
FIG. 7 is a rear view with adjustable fastening units closed on the protective helmet of FIG. 3.

FIG. 7 discloses a rear elevational view of a protective helmet 24 with the respective first adjustable fastener unit 44 and second adjustable fastening units 46 closed.

Figure 8:
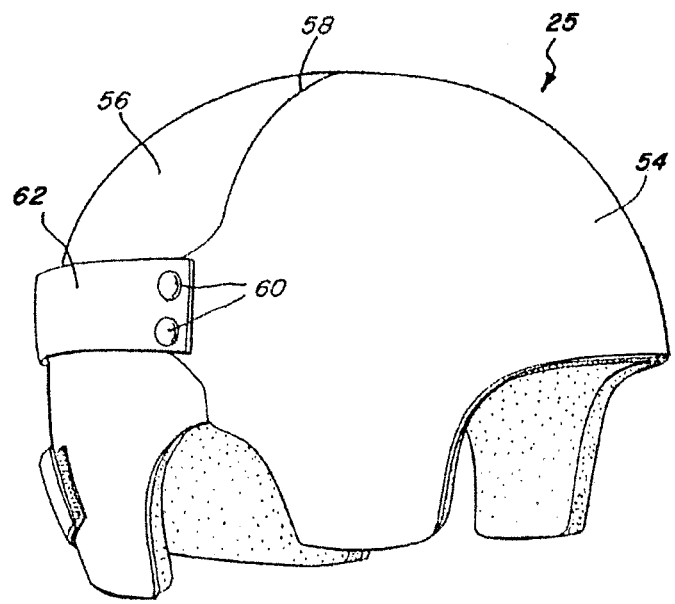
FIG. 8 is a modification of the embodiment of FIG. 3 with rivets and a modified parting trim line.

FIG. 8 is a front side perspective view of a modification of the protective helmet 24 wherein a protective helmet 25 is shown having a trim line between the first component 54 and the second component 56 so that the trim line 58 is indented with a pair of rivets 60 for attaching a fastening strip 62.

Figure 9:
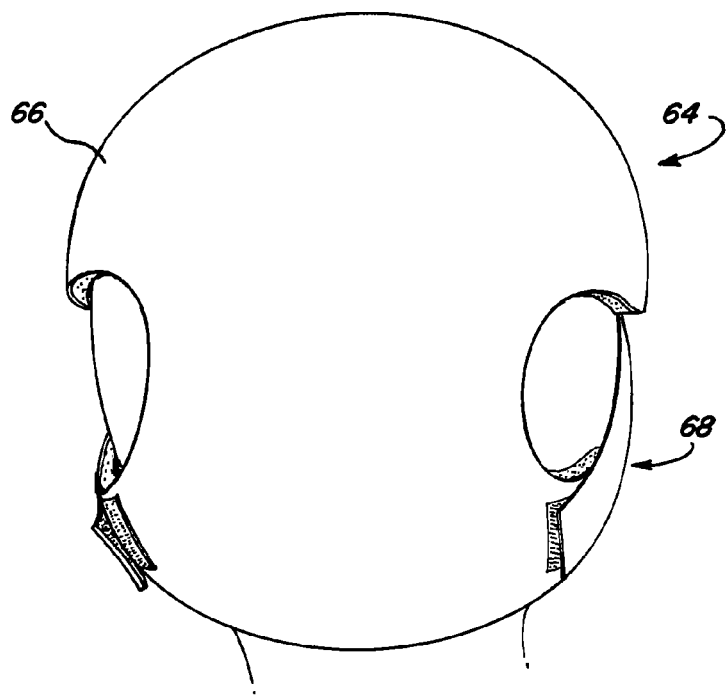
FIG. 9 is a rear elevational view of a protective helmet with open side lobes.
Figure 10:
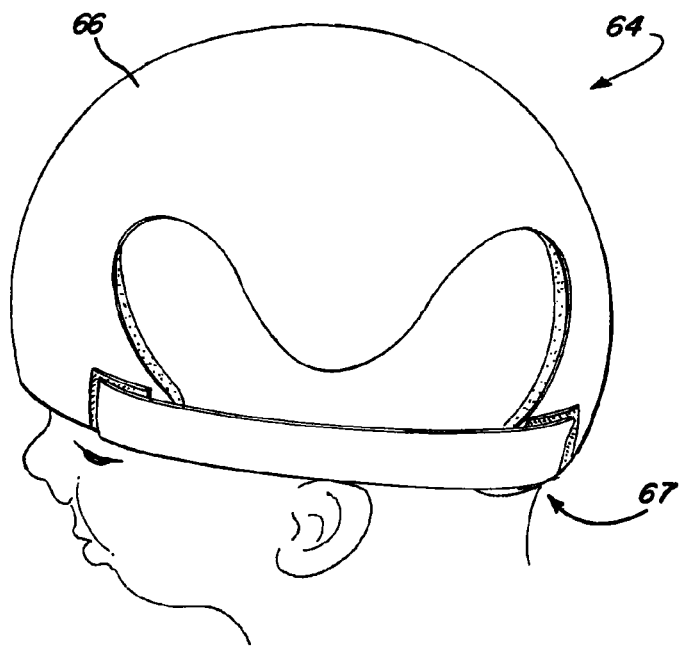
FIG. 10 is a side view of the protective helmet of FIG. 9.

FIGS. 9 and 10 disclose respectively a rear end side view of another embodiment of a protective helmet 64 having a relatively flexible unitary plastic shell component 66 with symmetrical curved openings of a curvilinear configuration to both accentuate the flexibility of the helmet while rendering it both lightweight with the capability of performing a monitoring of internal cranial pressure sensor for accessing the cranial cavity offset from the affected craniectomy site. Again, a pair of fastening units 67, 68 can be adjusted for securing the helmet 64 to the patient. The fastening unit 68 operates in a manner described with regards to the first embodiment with fastening straps and anchor patches.

Figure 11:
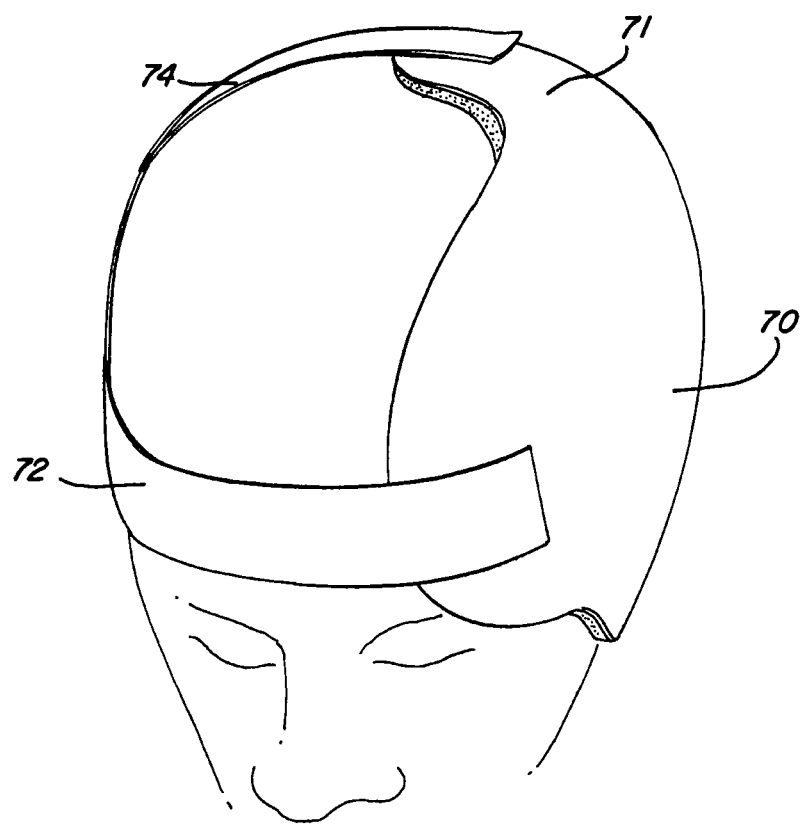
FIG. 11 is a unitary side protective helmet with a fastener unit of straps and anchoring patches of a nap and hook configuration.

FIG. 11 discloses a further variation of a unitary side protective shell with a cushioning liner having a semi annular strap that can be connected from a front across a side to a rear of the unitary side protective helmet 70 in the form of a band or strap 72 with an intermediate strap 74 connected to the strap 72 and adhered again through a Velcro™ patch directly to the top of the helmet 70. Note, the straps 72 and 74 can have an elastic capacity to ensure a secure but comfortable fitting to the patient's head.

This embodiment of a semi-protective shell provides a minimal cover of a craniectomy site on the left hand side of the patient, as shown in FIG. 11, thereby providing a lightweight helmet with access for monitoring in the rest of the exposed skull.

Figure 12:
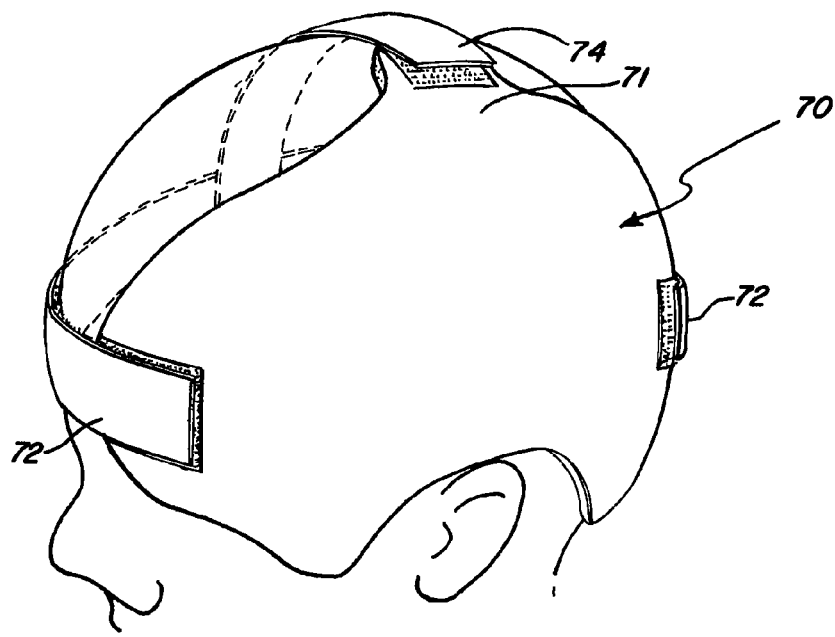
FIG. 12 is a side perspective view of the protective helmet of FIG. 11.

FIG. 12 is a side perspective view of the helmet 70 which covers, as shown in the drawing, half of the left side of the patient's skull. The helmet 70 has a trim perimeter extending across the head from the frontal bone through the parietal bone and occipital bone with a cantilevered anchor extension 71 for appropriately securing the strap 74 over the patient's head.

Figure 13:
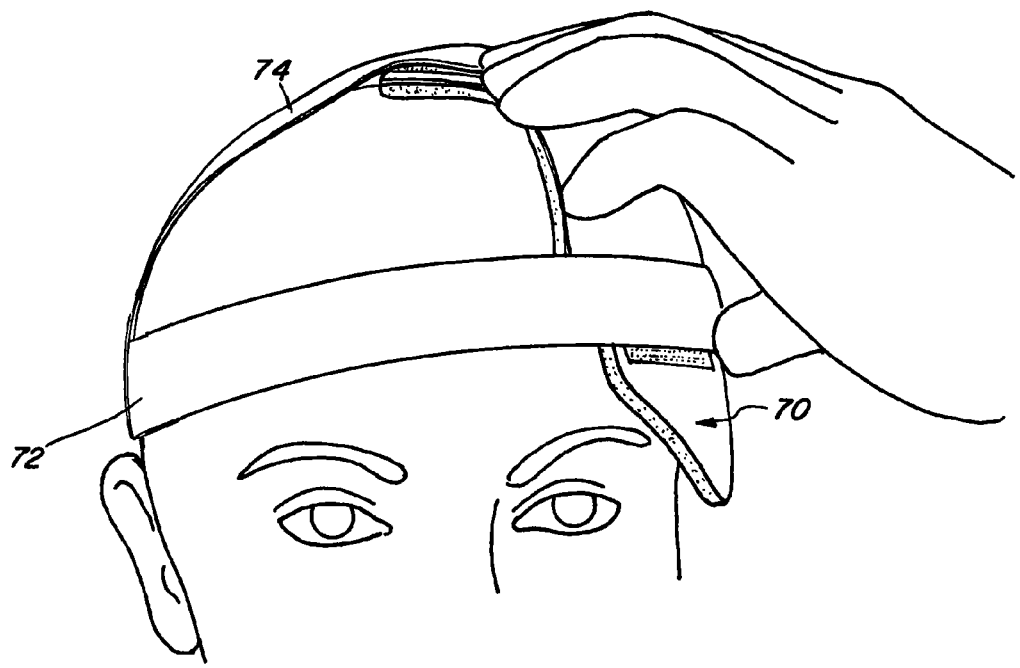
FIG. 13 is a front elevated view of the protective helmet of FIG. 11.

As can be seen in FIG. 13, the respective straps 72 and 74 can be attached to appropriate anchoring positions with adhesive patches having one of a nap or hook configuration that complements the respective hook or nap configuration used on the respective straps to provide first and second adjustable fastener units.

Figure 14:
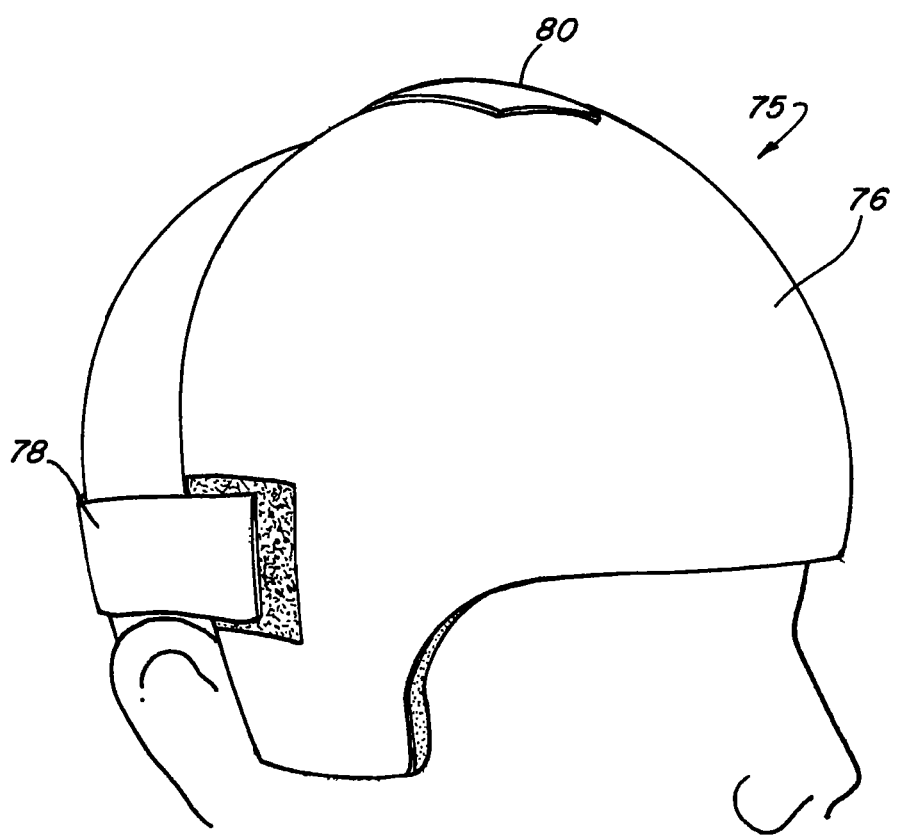
FIG. 14 discloses a protective frontal helmet cap with an encircling adjustable fastener unit.

FIG. 14 disclose a modification where a protective frontal helmet cap 75, again of an exterior plastic shell with an appropriate foam cushioning liner, forms a protective frontal shell 76. An encircling fastener strap 78 with an intermediate strap 80 extending upward from the encircling strap 78 is directly connected at the top of shell 76. The straps 78 and 80, can have an elastic stretch capability.

Figure 15:
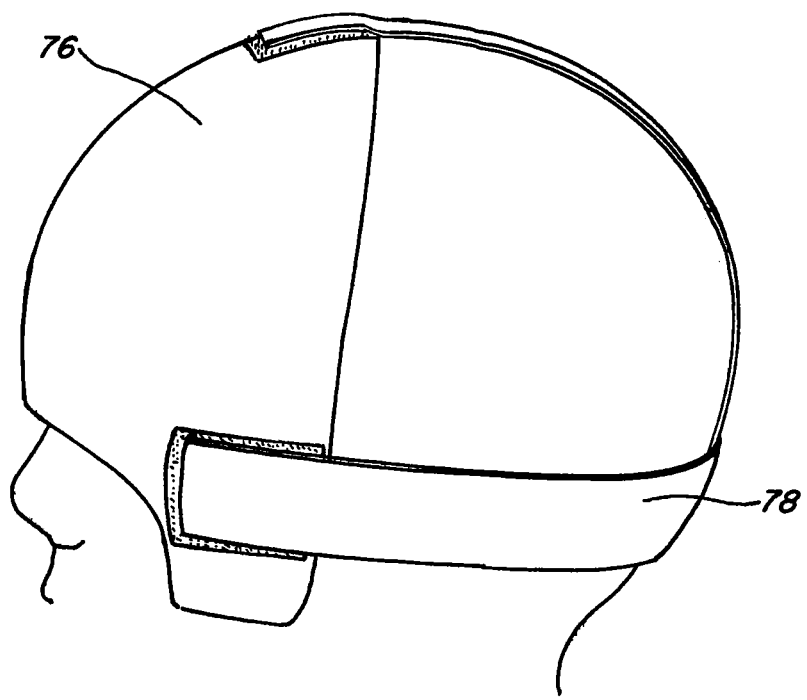
FIG. 15 is a side view of the protective helmet of FIG. 14.
Figure 16:
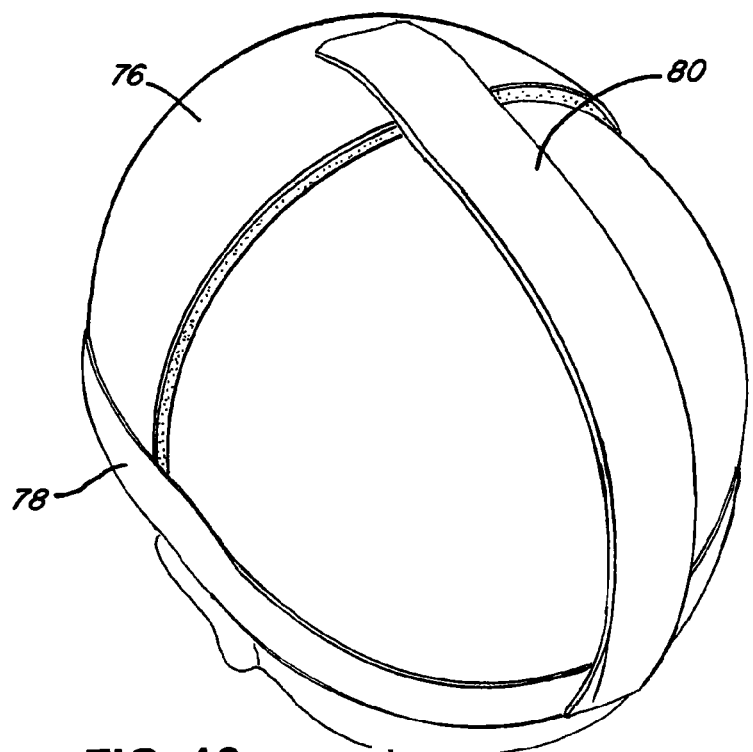
FIG. 16 is an upper perspective view of the rear of the protective helmet fastening straps of FIG. 14.

The frontal cap is seen from a perspective front view in FIG. 14 and from a side view in FIG. 15 and a rear view in FIG. 16.

Figure 17:
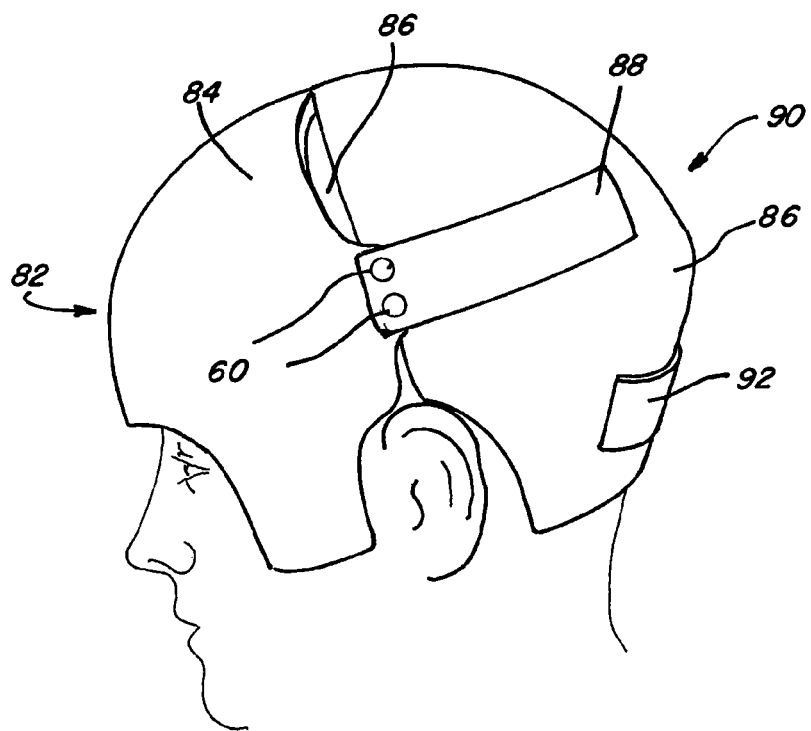
FIG. 17 is side view of a modification of the protective helmet shown in FIG. 8.

Another embodiment of a protective helmet 82 is shown in FIG. 17, and it is a modification of the embodiment shown in FIG. 8. It has the 60 for connecting a fastener strap 88 which is provided on both sides of the split first component 84 and second component 86, plus a pair of pair of first fastening units 90 are provided with a fastening strip 90 extending across the back that can also be provided with a teardrop opening in the same manner shown in protective helmet 24, shown for example in FIGS. 6 and 7. The modification in helmet 82 is the opening 96 that can be symmetrically provided on both sides of a living plastic hinge connecting the first front shell 84 and the second rear shell 86 at the top of the helmet 82 (which is not shown), along the trim line, that extends from one ear opening to the opposite ear opening on the patient. The trim line contains an opening slot 96 to permit access to the cranial cavity for monitoring the condition of the patient.

Figure 18:
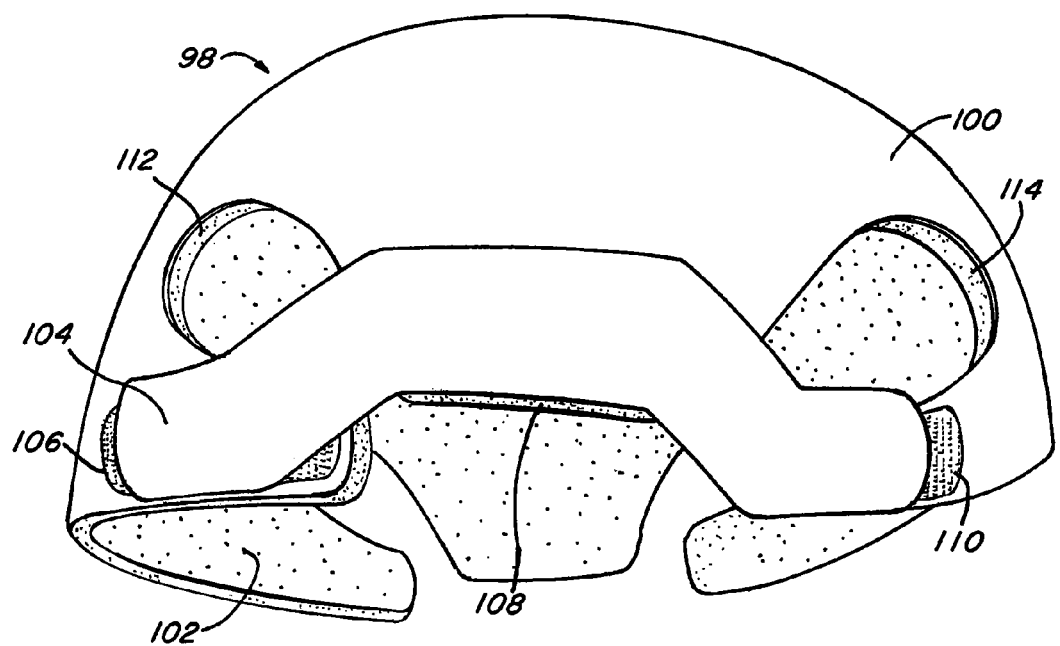
FIG. 18 is a protective helmet having open lobes and an adjustable fastening unit in a front elevational view.

FIG. 18 discloses an alternative protective helmet 98 having a plastic shell 100 with cushioning liner of foam 102. FIG. 18 represents a frontal view of the protective helmet 98 and discloses a first adjustable fastener unit for extending across a frontal bone with respective anchoring patches 106, 108 and 110. A fastening strap 104 can have one of a nap or a hook configuration while the anchoring patches 106, 108 and 100 can have a complementary nap or a hook configuration to permit an adjustable attachment. As can be determined, a pair of open lobes 112 and 114 are symmetrically arranged in the protective helmet 98 to provide flexibility to the front portion of the protective helmet 98. A trim line below the lobes 112 and 114 provides a cantilevered section of the helmet with respective anchoring patches 106 and 110 while the lower central portion projects downward in the front of the helmet 98 and mounts another anchoring patch 108.

Figure 19:
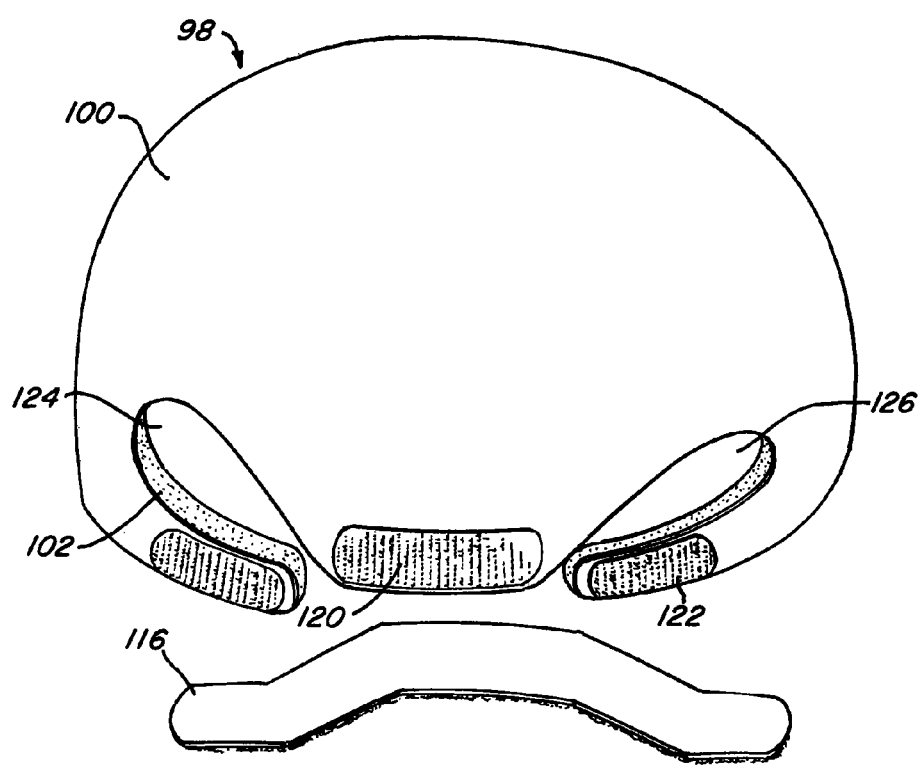
FIG. 19 is a rear elevational view of the protective helmet of FIG. 18 with rear lobes and the rear adjustable fastener unit.

As can be seen in FIG. 19, a somewhat similar configuration of lobes 124 and 126 are disclosed at the rear of the helmet 98 to provide flexibility for securing the protective helmet 98 along a trim line for fastening it to the user's head. A second adjustable fastening unit also includes respective anchoring patches 118, 120 and 122 with a fastening strap 116 of a nap and hook configuration. The respective lobes 124 and 126 aid in providing flexibility as in the frontal portion of the helmet for a flexible but secure mounting on the user's head.

Figure 20:
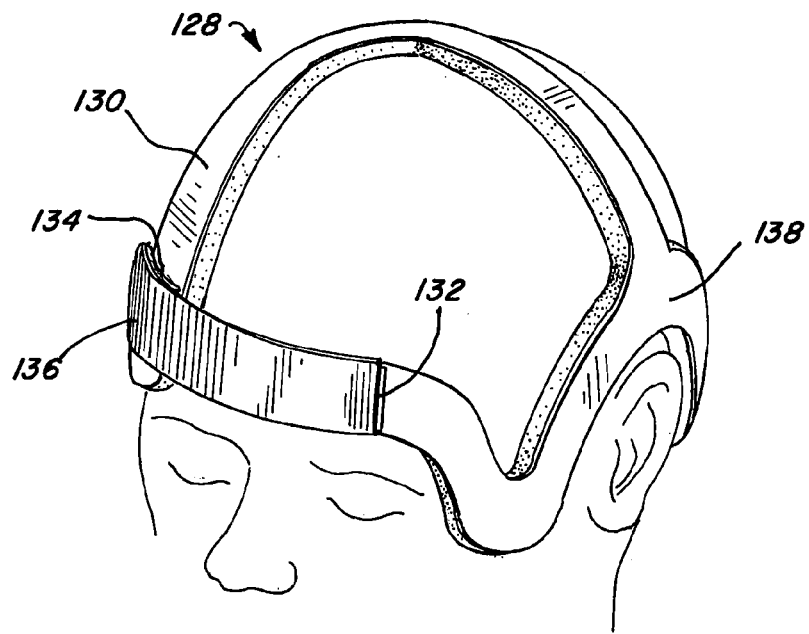
FIG. 20 is a perspective view of a protective helmet for protecting one side of a patient with an open lattice support structure on the other side.
Figure 21:
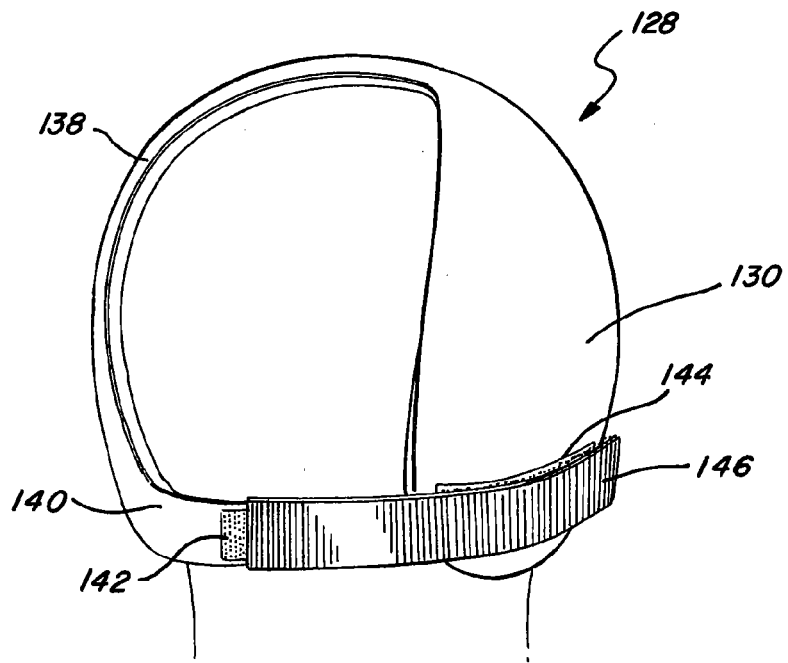
FIG. 21 is a rear elevational view of the protective helmet of FIG. 20 with an adjustable fastener unit shown.

FIGS. 20 and 21 disclose another embodiment of a protective helmet 128 designed to cover from a frontal bone across a right side of the patient's parietal bone and occipital bone to protect a craniectomy surgical site on the right side of the patient's head while leaving a substantial portion of the rest of the skull accessible for both ventilation purposes and monitoring, such as an intracranial pressure transducer that can be used to both monitor the pressure within the cranial cavity and release fluid apart from the affected craniectomy site.

The protective helmet 128 conforms to the right side of the skull of the patient with an exterior plastic shell with a degree of flexibility and an interior cushioning liner, as in the other embodiments, with a half shell 130. Mounting anchor patches 132 and 134 are provided for an adjustable fastener unit with an elastic fastening strap 136 that can extend across the forehead or frontal bone of the patient to attach to the respective anchoring patches 132 and 134. The cantilevered support structure on the left side of the patient is a unitary continuation of the shell 130 and forms a latticework or support structure 138. Since the support structure 138 has a curvilinear configuration for both firmly attaching and supporting the half shell 130, it provides an inverted Y configuration that is open both on the front and on the back and spaced from the half shell 130.

As seen in FIG. 21, the rear of the half shell is open with a flexible cantilevered portion 140 extending partly across the occipital bone and having an anchor patch 142 for securement to an elastic fastening strap 146 to provide a second adjustable fastener unit. An anchor patch 144 is mounted adjacent the edge of the half shell 130 above the trim line. As can be readily appreciated, there are significant opening spaces to permit monitoring sensors and relief of any cranial fluid in this embodiment.

FIGS. 22-25 represent a variation of the embodiment of FIGS. 20 and 21. Again, a half shell 148 is provided on the right side although it should be appreciated that it is possible to provide the same configuration of a protective helmet for the left side of a patient. A separate shell component 150 completes the protective helmet 152. As can be seen in FIG. 23, the shell component 150 has approximately an inverted Y shape with the lower perimeter having a curve to accommodate the ear of the patient and to provide an anchor point for anchor patches 154 and 156.

The lower perimeter of the support shell 150 is designed to capture the head of the patient to prevent rotation or migration of the protective element while a central curved cantilevered support member 158 extends halfway over the user's head. As can be seen in FIG. 24, the support member 158 can be positioned adjacent to or in contact with an outwardly bulging convex central portion of the half shell 148.

As with the other embodiments of the present invention, a hard exterior plastic shell is lined with a closed cell foam to provide a cushioning layer.

A first adjustable fastener unit includes the fastening strip 162, the anchor patches 160 and 154. A second adjustable fastener unit includes, at the rear of the protective helmet 152, a fastener strap 166 and anchor patches 156 and 164 as shown in FIG. 25.

Figure 22:
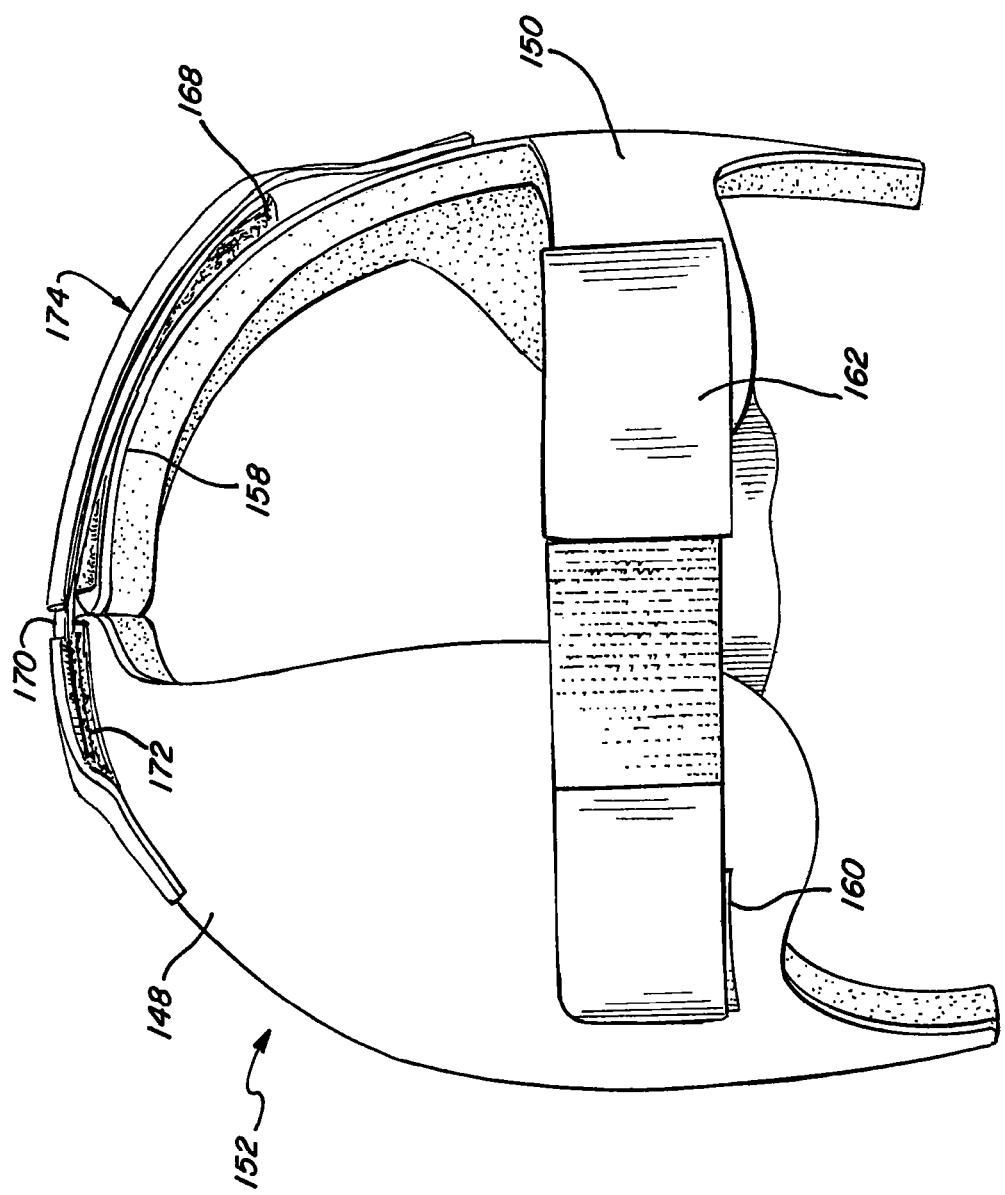
FIG. 22 is a front elevational view of a protective helmet having two component shells.

A third adjustable fastener unit is mounted across the top of the protective helmet 152 and includes a fastener strap 170 that can be connected to an anchor patch 168 and an anchor patch 172. The fastener strap 170 can further incorporate a semi-rigid plastic band to provide a stable unitary connection between separate shell components It is also possible to provide, in the different embodiments of the protective helmets, a further separate security fastener strap 174 that can be mounted over the appropriate fastener strap, for example as shown in FIG. 22 at the top, to thereby provide an additional locking component for maintaining the stability of the protective helmet 152. The overlying strap 174 would have appropriate nap or hooks to provide an additional layer of security and connection above the fastening strap 170.

FIG. 26 represents a schematic of a human skull with removed a bone to provide a decompressed injury site 22.

FIG. 27 is a schematic representing a patient with a dressing over the injury site.

FIGS. 28-30 disclose a full cranial protective helmet with a right side plastic shell or component 178 and a left side protective shell or component 180. A living hinge 182 connects the respective shells 178 and 180 and permits them to rotate to an open or spread position. A first adjustable fastener unit can include a strap 184 extending partially across the frontal bone and a rear strap 186 extending partially across the occipital bone. Anchor patches are provided appropriately on each of the half shells 178 and 180 and one anchor patch 188 is shown in FIG. 29 as representative.

As can be appreciated, the combination of the front fastening strap 184 and appropriate anchor patches can form a first adjustable fastener unit while the fastening strap 186 and the anchor patch 188 can form the second adjustable fastening unit. The respective fastening straps 184 and 186 can be relatively elastic.

Optionally a chin strap arrangement 190 can also be provided with an adjustable buckle for further securing the protective helmet 176 on the patient. as shown in FIG. 28, with appropriate measurements of the location of the injury site 22, for example by an optical scan, the protective helmet 176 can be appropriately formed to include an elevated segment 192 for both an exterior plastic shell and the closed foam cushioning liner, thereby accommodating the elevation of dressings or bandages 194. For example, a half inch area around the injury site 22 can be provided on the helmet and the helmet itself can be raised to provide a space of approximately ½ inch to accommodate the dressing 194, thereby preventing any additional pressure to be asserted on the injury site. Ventilation holes 196 can be provided throughout the helmet.

In operation, the respective shells 178 and 180 can be spread by rotating about the living hinge 182 and thereby facilitate a carefully placing of the helmet over the bandaged injury site 22. The respective fastening straps 184 and 186 can be adjusted and if necessary, an auxiliary chin strap can be applied to further secure the protective helmet 176 on the patient.

Figure 31:
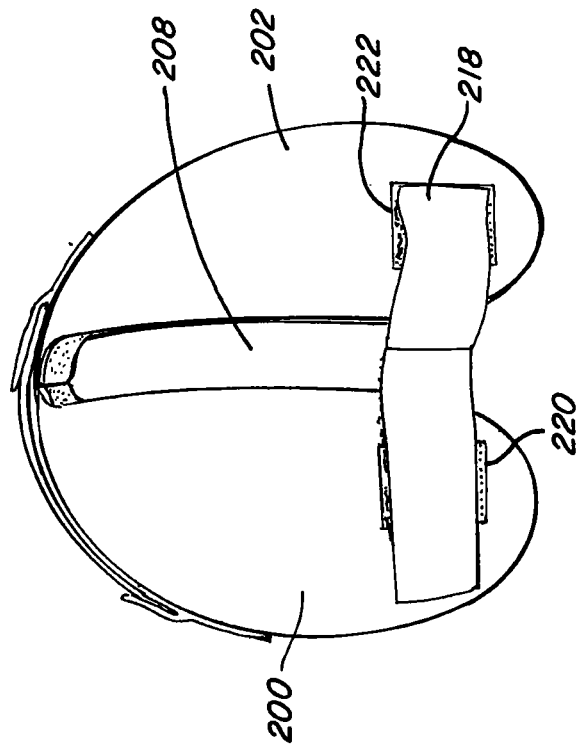
FIG. 31 is a frontal view of a bilateral protective helmet.

A bilateral split cranial protective helmet 198 is shown in a front elevated view in FIG. 31 and includes a left half shell 200 and a right half shell 202. Both exterior plastic shells (and a closed cell foam cushioning liner) are similar with regards to the other helmet embodiments. The respective shells 200 and 202 have a symmetrical trim line as can be seen from the bottom view of FIG. 31 with the cushioning liners 204 and 206 on the respective shell.

Figure 34:
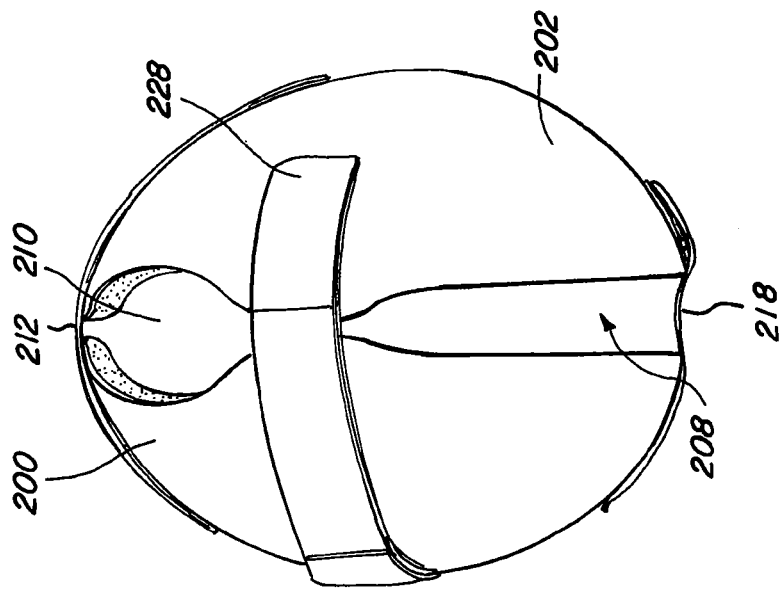
FIG. 34 is a top plan view of the protective helmet of FIG. 31.
Figure 33:
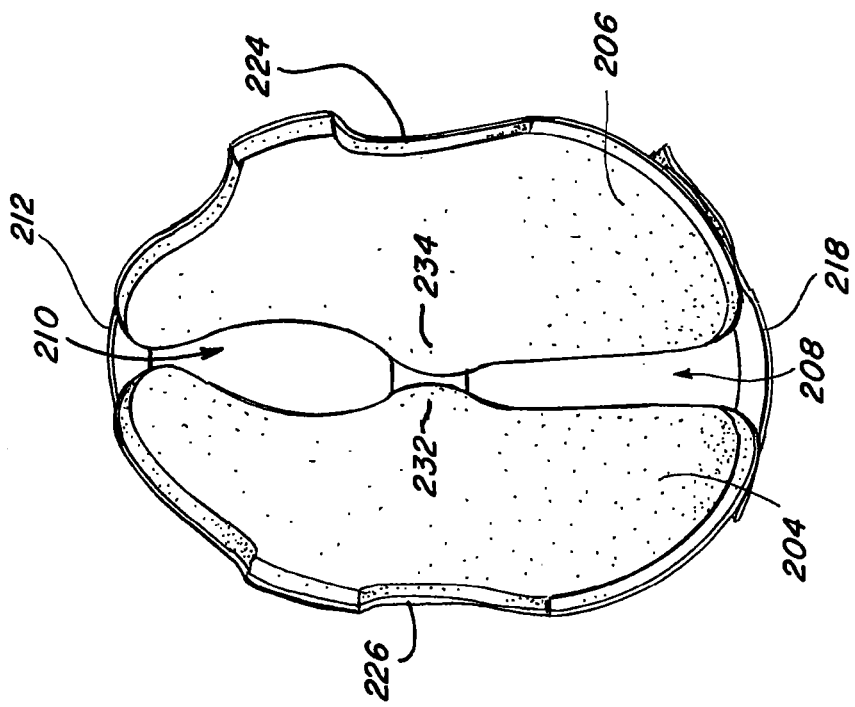
FIG. 33 is a bottom plan view of the protective helmet of FIG. 31.

A rear elongated slot 208 is formed between shells 200 and 202 with a tear drop opening 210 formed in the front of the protective helmet 198. FIG. 34 shows a plan view of the bilateral protective helmet 198. A first adjustable fastener unit having an elastic fastener strap 212, can be adjustably connected to appropriate anchor patches 214 on the left shell 200 and anchor patch 216 on the right shell 202. As with the other embodiments, an appropriate nap and hook arrangement can be provided relative to both the fastener straps 212 and the anchor patches 214 and 216.

Figure 32:
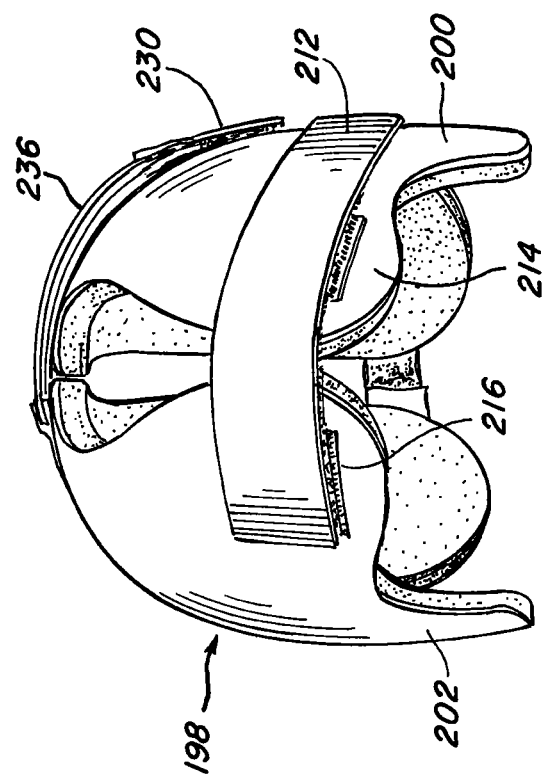
FIG. 32 is a rear elevated view of the protective helmet of FIG. 31.

A second adjustable fastener unit can be provided in a similar manner as shown in FIG. 32, at the rear of the helmet adjacent the trim line. An elastic fastener strap 218 capable of being attached to anchor patches 220 and 222.

The respective sides of each of the shells 200, 202 have concave perimeter openings to provide ear openings 224 and 226.

A third adjustable fastener unit includes an anchor patch 230 for securing a strap attached to the right shell 202 to extend over the respective convex trim portions 232 and 234 at the middle portion of the opposing shell trim lines as shown in FIG. 34. A security strap 236 can further lock the respective right shell 202 and left shell 200 together so they can rotate to an open position for easy mounting on the patient's head.

The open approximate rectangular slot 208 and the teardrop opening 210 are available to assist in any monitoring, for example with an intracranial pressure transducer to determine the pressure and to relieve fluid. The respective shells have a sufficient flexibility to conform to variations of the cranial shapes and the underlying bandages, if any. The respective trim lines, both on the perimeter along with the rectangular slot 208 and teardrop opening 210 assist in providing an anti-rotation of the helmet as well as the adjustable strap fasteners. As seen in the other helmet embodiments and as employed on the trim line of this bilateral protective helmet 198, the temporal extensions and ear cut outs on the trim line also help prevent any rotation or migration of the helmet 198.

The bilateral protective helmet 198 is frequently used when a patient is lying face upward while unilateral protective helmets, where only one side of a protective shell is utilized, utilize the posterior trim lines designed to permit the patient to lie face up without putting excessive rotational pressure on the device. The bilateral protective helmet 198 has a posterior trim line designed symmetrical to also reduce rotational forces.

As can be appreciated, the bilateral protective helmet 198 as well as the other embodiments disclosed herein, can either be produced in prefabricated sizes or could be custom fit using CT scan images or any other scanning device to provide accurate measurements of the topography of a patient's skull. As can be appreciated, an orthotist can fit and trim each of the respective protective helmets disclosed in our Figures to match requirements that could be subjective to the respective patients. The security or tamper resistant straps can overlay the proper adjustment by the orthotist and thereby discourage tampering by the patient. The adjustable fastener units are generally adjusted to provide equal pressure on both the anterior and posterior of the protective helmets and an optional chin strap shown, for example, in FIG. 30, can also be added as a modification to many of the embodiments.

In the two component protective helmets, where each portion of the helmet is a separate component that are brought together and united by fastening bands or straps, security fastener strips can be used to provide additional security against an accidental or intentional unfastening to increase the safety for the patient.

Figure 35:
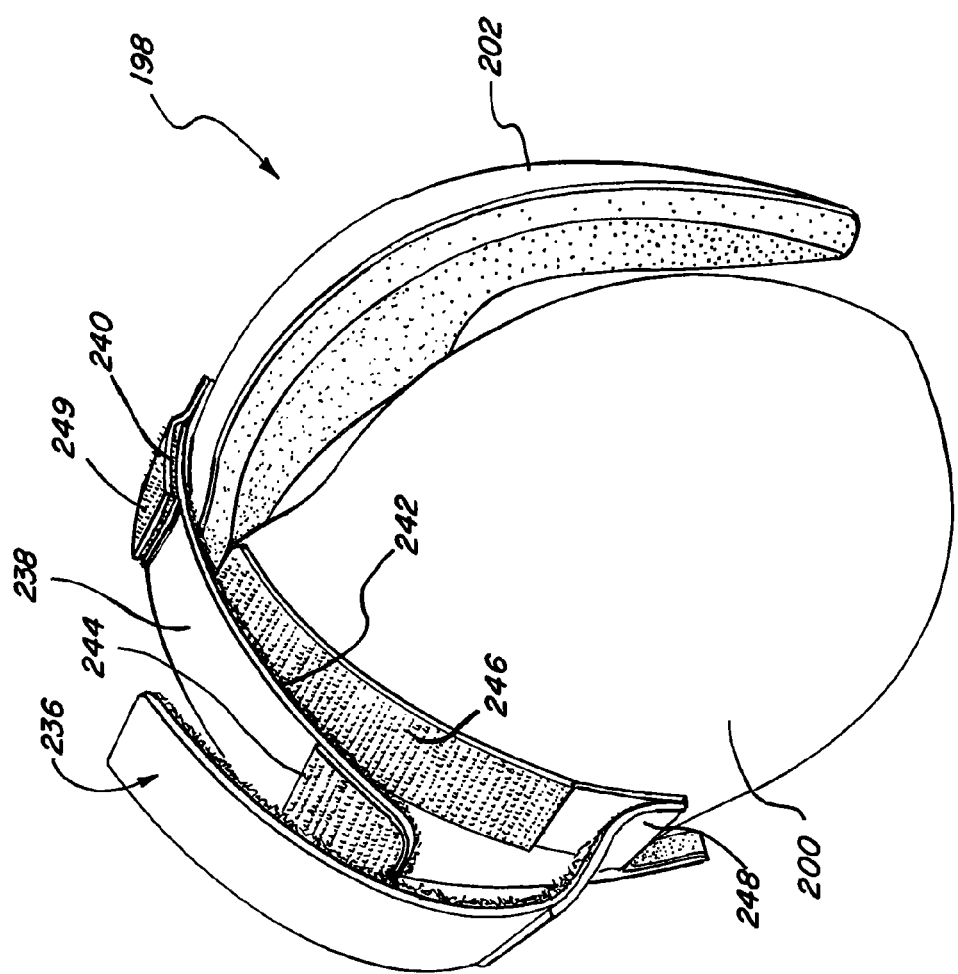
FIG. 35 is a view of a protective helmet having a modified strapping system with a semi-rigid plastic strap.

Referring to FIG. 35, the bilateral protective helmet 198 is shown with a modification of an intermediate adjustable fastener unit extending across the respective left helmet shell 200 and the right helmet shell 202. The modification involves adding a semi-rigid polyethylene plastic strap 238 that can be pivotally mounted within an anchor sandwich of nap and hook material 240 that is affixed adjacent the convex trim portion 234 of the right shell 202. This semi-rigid strap 238 is movably anchored in the sandwich of nap and hook material that is adhered to the outer surface of the shell 202. The semi-rigid plastic strap 238 has an under surface of nap material 242 adhered by an adhesive to the semi-rigid plastic strap 238. At the respective ends 244 of the plastic strap 238 are anchor patches 244 and 249 of hook material.

The left shell has an extended anchor patch of hook material 246. At the distal end of the hook anchor patch 246, an elastic strap 248 of nap material is fastened to the distal end of the hook patch 246. In operation, the left shell 200 and right shell 202 are mounted on the patient's head and equal pressure is applied by the first adjustable fastening unit across the frontal bone and a second fastening unit across the occipital bone of the user. The position of the left shell 200 and the right shell 202 is then securely maintained by applying the semi-rigid plastic strap 238 for connection with the anchor hook patch 246. The elastic strap 248 is then extended across the semi-rigid plastic strap 238 to act as a security strap 236 for connection with the hook patches 244 and 249.

Figure 36:
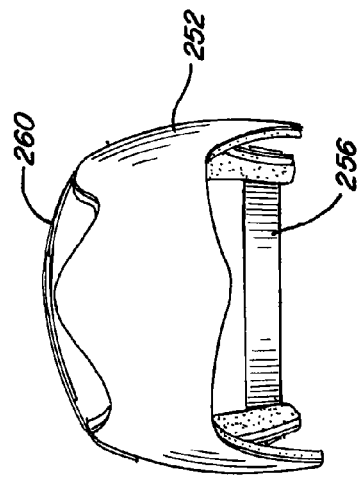
FIG. 36 is a bi-frontal protective helmet.
Figure 37:
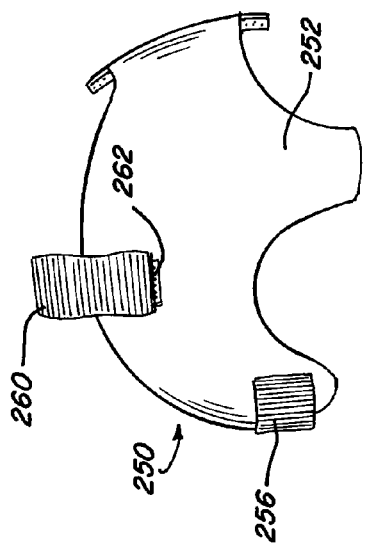
FIG. 37 is a bottom plan view of the protective helmet of FIG. 36.

FIG. 36 is a side view of a protective helmet 250 with an open top in a U-shape configuration as can be seen in FIG. 37. Accordingly, a curved flexible exterior plastic shell 252 of a generally U-shaped curved configuration with a foam cushion liner 254 is provided with an elastic fastening strap 256 that is appropriately attachable to an anchor patch 258 at the distal end of the fastening strap 256. The strap can be appropriately anchored to the plastic shell 252 by rivets or an anchor patch (not shown).

An upper adjustable fastener unit extending across a portion of the plastic shell 252 and the opening is a fastening strap 260 that can be anchored onto the anchor patch 260. The respective fastening straps 256 and 260 can be a combination of elastic material and a non-stretchable fastening section which would be complementary to one of either hook or nap on the anchor patches. An example of fastening strap material is a Velstretch™ Brand Tape 151 of nylon and elastomer manufactured by Velcro™ Corporation.

Figure 38:
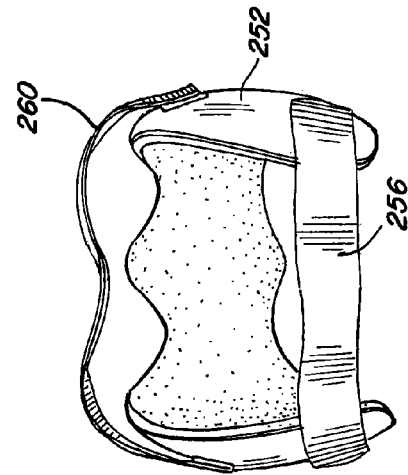
FIG. 38 is a front elevated view of the protective helmet of FIG. 36.
Figure 39:
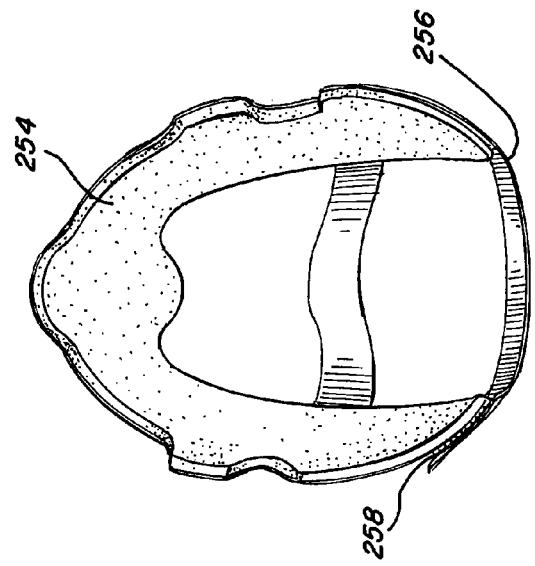
FIG. 39 is a rear elevated view of the protective helmet of FIG. 36.

As seen in FIGS. 38 and 39, the plastic shell 252 and the foam cushion liner 254 have a sinusoidal perimeter where there is increased coverage over the frontal bone at the front of the protective helmet 250. The protective helmet 250 would be designed for an injury site on the frontal bone or the sides of the parietal bones. The trim line around the ears and the side of the plastic shell are to facilitate securement of the plastic helmet 250 to the skull of the patient.

As can be appreciated from the various embodiments of a protective helmet, features used in one helmet can be frequently applied to the other helmets as discussed in the body of our application. As can be appreciated, living hinges can be replaced by separate hinge components and the plastic shells can be made of various compositions of resin as long as they provide sufficient rigidity to protect against low impact forces while providing flexibility for mounting on and accommodating the comfort of the patient whether ambulatory or by necessity lying in a bed during a recuperation after a craniectomy.

Our protective helmets not only address the comfort and security of the patient, but also facilitate the monitoring with sensors of the condition of the patient while facilitating the changing of any bandages with minimal disturbance of the patient.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. A medical cranial protective helmet consisting of:
a hemispherical exterior hard plastic shell that is flexible to enable sizing adjustment on a user and an interior hemispherical interior cushioning laminated into the hemispherical exterior hard plastic shell as a liner;
the hemispherical exterior hard and flexible plastic shell has a hinge formed integral with the hemispherical exterior hard and flexible plastic shell and adjacent the hemispherical interior cushioning liner at a top of the hemispherical exterior hard and flexible plastic shell to permit the cranial protective helmet to be divided to enable sizing adjustments on the user as follows,
   a first helmet component having a first exterior hard and flexible plastic shell and a first interior cushioning liner adapted to conform to a portion of an outside surface of a user's head from a frontal bone to a parietal bone, and
   a second helmet component having a second exterior hard and flexible plastic shell and a second interior cushioning liner adapted to confirm to a portion of an outside surface of a user's head from the parietal bone to an occipital bone, wherein the first and second components are connected together by the integral hinge on an exterior surface of the first and second helmet components and the first and second helmet components rotate about the integral hinge to a spread open position for insertion on a user's head and close together to protect the user's head when the hemispherical exterior hard and flexible plastic shell with the interior hemispherical interior cushioning liner is secured to the user's head;
a first adjustable fastener unit, extending across a portion of the first helmet component and a portion of the second helmet component adapted to permit a sizing adjustment to the user;
a second adjustable fastener unit, extending across a portion of the first helmet component and a portion of the second helmet component adapted to permit a sizing adjustment to the user; and
a third adjustable fastener unit, extending across a portion of the second helmet component in a location between the first and second adjustable fastener units to enable a sizing adjustment of a perimeter trim line of the second helmet component exterior hard and flexible plastic shell and the laminated interior cushioning that is to be adapted to extend adjacent the occipital bone,
wherein the perimeter trim line extends upward into the second helmet component to form an upper hemispherical opening through the rear of the second component hard and flexible plastic shell and the interior laminated cushioning liner and the third adjustable fastener unit is positioned to extend across the perimeter trim line and the upper hemispherical opening and adapted to enable a partial closing of the upper hemispherical opening of the hard and flexible second helmet component to provide retention of the cranial protective helmet on the user's head by enabling the perimeter trim line to be adjusted on the user's head,
wherein the first helmet component and second helmet component have respective curvilinear perimeter surfaces that are opposite to each other and together form opposed spaced openings, each of a size to be adapted to be aligned over the user's head, for extending around a respective user's ear, and
wherein the first, second and third adjustable fastening units each include a strap with one of a hook or a nap complementary fastening element.

2. The medical cranial protective helmet of claim 1 wherein the hemispherical exterior hard and flexible plastic shell is formed from a plastic copolymer with a tension strength of approximately 3100 psi, a durometer hardness of 60, a tension elongation before breakpoint of 240% and is adapted to provide both protection to the user's head and resiliency to provide retention of the cranial protective helmet on the user's head.

3. The medical cranial protective helmet of claim 1 wherein each of the first, second and third adjustable fastener units include the strap attached at one end to an outer surface of the hemispherical exterior hard and flexible plastic shell and a hook component attached to the other end of the flexible strap for fastening to a nap component positioned on the outer surface of the hemispherical exterior hard and flexible plastic shell.

4. The medical cranial protective helmet of claim 1 wherein an open space extends from opposite side of the integral hinge from the top of the hemispherical exterior hard and flexible plastic shell to the perimeter trim line to permit relative rotation of the first and second helmet components.

* * * * *